United States Patent [19]

Tomalia et al.

[11] Patent Number: 4,713,975

[45] Date of Patent: Dec. 22, 1987

[54] DENSE STAR POLYMERS FOR CALIBRATING/CHARACTERIZING SUB-MICRON APERTURES

[75] Inventors: Donald A. Tomalia; Larry R. Wilson, both of Midland, Mich.

[73] Assignee: The Dow Chemical Company, Midland, Mich.

[21] Appl. No.: 868,979

[22] Filed: May 30, 1986

[51] Int. Cl.$^4$ .................. G01N 33/00; G01N 33/483; G01N 15/08

[52] U.S. Cl. ....................... 73/865.8; 73/38; 73/866; 210/644; 435/4; 435/5

[58] Field of Search ............ 73/865.8, 866, 38, 865.5; 210/644, 649-652, 653; 435/4, 5

[56] References Cited

U.S. PATENT DOCUMENTS

| | | | |
|---|---|---|---|
| 2,693,706 | 11/1954 | Carpenter et al. | 73/865.5 |
| 3,392,573 | 7/1968 | Benson et al. | 73/38 |
| 3,455,146 | 7/1969 | Smith et al. | 73/38 X |
| 3,478,601 | 11/1969 | Niebergall | 73/38 X |
| 4,507,466 | 3/1985 | Tomalia et al. | 528/363 X |
| 4,558,120 | 12/1985 | Tomalia et al. | 528/363 |
| 4,568,737 | 2/1986 | Tomalia et al. | 528/363 X |
| 4,586,376 | 5/1986 | Outmans | 73/866 X |
| 4,599,400 | 7/1986 | Tomalia et al. | 528/403 X |
| 4,648,261 | 3/1987 | Thompson et al. | 73/38 |

OTHER PUBLICATIONS

N. Unwin and R. Henderson, Feb. 1984, The Structure of Proteins in Biological Membranes, Scientific American, pp. 78-94.

Charles F. Stevens, Biophysical Studies of Ion Channels, pp. 1346-1350; Science.

H. K. Lonsdale, The Growth of Membrane Technology (1982), Journal of Membrane Science, vol. 10, pp. 81-181.

Membrane Technology, D. R. Paul and G. Morel, Chemical Technology, (1981), vol. 15, pp. 92-131.

*Primary Examiner*—Tom Noland
*Attorney, Agent, or Firm*—Joseph T. Majka

[57] ABSTRACT

In a substance such as a membrane, a cell or virus having at least one aperture of a diameter of about 10,000 Angstroms or less, a process for measuring and characterizing the diameter of the aperture, comprising:

(a) contacting the substance with a solution of a plurality of dense star polymers;

(b) passing through or into the aperture at least one dense star polymer having a molecular diameter of about equal to or less than the diameter of the aperture; and (c) calculating the diameter of the aperture from measurements of either those dense star polymers passing therethrough or thereinto the aperture, of those dense star polymers not passing therethrough or thereinto, or of the combined measurements of those dense star polymers passing therethrough or thereinto the aperture and those not passing therethrough or thereinto.

18 Claims, No Drawings

DENSE STAR POLYMERS FOR CALIBRATING/CHARACTERIZING SUB-MICRON APERTURES

FIELD OF THE INVENTION

The present invention relates to processes for calibrating and characterizing substances having apertures ranging between about 8 to about 10,000 Angstroms (Å), including substances which are natural or synthetic membranes, or are discrete biological particles such as viruses, enzymes or proteins.

BACKGROUND OF THE INVENTION

In the past two decades numerous technological advances in the medical and biological arts have prompted a better understanding of the micro-universe, or that which cannot be seen with the naked eye. Methods are known for calibrating and characterizing apertures in the range between 0.1 micron ($\mu$) to 10$\mu$ (1000 Angstroms (Å) to 100,000 Å where 1$\mu$=10,000 Å).

This range covers the sizes and shapes of most bacteria, such as Rickettside and Mycoplasma sp. (1000–3000 Å), *Hemophilus influenzae* (2000–3000 Å,×5000–20,000 Å), *Escherichia coli* (5000×10,000–30,000 Å) *Bacillus anthracis* (10,000–13,000×30,000–100,000 Å) and also blood cells (~700,000 Å). In comparison, the limit of human vision is about 400,000 Å.

These known methods, however, are unsatisfactory for calibrating and characterizing even smaller apertures, such as those having diameters from 0.1$\mu$(~1000 Å) to 0.001$\mu$(10 Å). Within this size range are measured discrete biological particles including viruses such as Reo virus and the pathenogenic Poliomyelitis virus responsible for polio (~310 Å); the stunted bean virus (~200 Å); the influenza virus (~1000 Å); important proteins such as insulin (diameter ~50–60 Å); the oxygen-carrying hemoglobin molecule found in blood cells (diameter ~80–100 Å); $\beta$-lipoproteins (diameter~200 Å) and other diverse subcellular components such as biological channels made of membrane proteins which allow nutrients, ions and other essential materials into plant or animal cells. Such membrane proteins are discussed in N. Urwin and R. Henderson, (Feb. 1984), The Structure of Proteins in Biological Membranes, Scientific American, pp. 78–94.

Present techniques for calibrating or measuring the apertures of such channels have met with only limited success because of the difficulty of designing a spherical structure as small as, for example, a cell channel (~15–20 Å). For example, such known processes employ structures which are random coiled and tend to reptate or unravel when contacted with an aperture of a size smaller than the measuring structure. This reptating or unraveling of these measuring structures, in turn, induces tremendous variations in measurements, requiring weeks and even months to perform. Such known measuring structures include nonspherical, low molecular weight compounds and proteins. For example, dextrans, a type of low molecular weight sugar, are subject to reptating motions through a pore whose dimensions are smaller than that of the dextran molecule. The dextran molecule uncoils and "snakes" through. The use of such deformable molecules as probes leads to serious doubt as to the validity of the measured molecular diameters.

Thus, it would be highly desirable to provide a precise, accurate and reliable process for calibrating and characterizing substances having submicron apertures.

SUMMARY OF THE INVENTION

In its broadest aspect, the present invention is a process for measuring and characterizing, in a substance having at least one aperture of about 10,000 Å or less, the diameter of the aperture. The process comprises the steps of:

(a) contacting said substance with a plurality of dense star polymers having at least one core branch emanating from a core, each core branch having at least one terminal group provided that (1) the ratio of terminal groups to the branches emanating from the core is 2:1 or greater, (2) the density of terminal groups in the dense star polymer is at least 1.5 times that of an extended conventional star polymer having similar core and monomeric moieties and a comparable molecular weight and number of core branches wherein each of such branches of the extended conventional star polymer bears only one terminal group, (3) a molecular volume that is equal to or less than 80 percent of the molecular volume of said extended conventional star polymer, and (4) the two-demensional molecular diameter of the dense star polymer is in the range from about 8 to about 10,000 Å;

(b) passing through or into said aperture at least one dense star polymer having a molecular diameter of about equal to or less than the diameter of said aperture; and (c) calculating the diameter of said aperture from measurements of either those dense star polymers passing through or into said aperture, of those dense star polymers not passing through or into, or of the combined measurements of those dense star polymers passing through or into said aperture and those not passing through or into.

In a somewhat more limited and preferred embodiment, the invention encompasses a method for measuring apertures whose two-dimensional molecular diameter ranges from about 8 to about 500 Å using the dense star polymers, more preferably between about 8 to about 100 Å. In substances having apertures whose molecular diameters range from about 40–500 to about 10,000 Å, the process of the present invention can utilize covalently bridged dense star polymer and dendrimer molecules. Between the range of 40–500 Å either dendrimers or covalently bridged dendrimers can be advantageously employed. While there is virtually no limit to the number or type of substances whose apertures can be measured and characterized by the present invention, the claimed process is particularly well adapted for measuring and characterizing apertures in synthetic and natural membranes. The process of the present invention is particularly useful in conjunction with hyperfiltration and ultrafiltration procedures.

The process of the present invention can also be used to characterize surfaces of discrete biological particles, such as viruses, bacteria and proteins, including enzymes.

For example, the process of the present invention can be used to map the surface apertures (i.e, antigen sites) of a discrete biological particle such as a cell, a virus, an enzyme, a protein or a bacteria for the purpose of matching or neutralizing conjugate antibody surfaces. Such information derived therefrom can be used to design and construct anti-viral agents. Such fractal surfaces are described in M. Lewis and D. C. Rees, *Fractal Surfaces of Proteins*, Science, 6 Dec. 1985, Vol. 230, pages 1163–1165, incorporated herein by reference.

As indicated supra, in substances having apertures whose molecular diameters range from about 40 to about 10,000 Å, novel covalently bridged dense star polymers or dendrimers can be employed for calibration. Hence, the present invention also provides a dense star polymer which is a dense star polymer covalently bridged to at least one other dense star polymer through at least one terminal group of each dense star polymer, wherein each dense star polymer has at least one core branch emanating from a core, each core branch having at least one terminal group provided that (1) the ratio of terminal groups to the branches emanating from the core is 2:1 or greater, (2) the density of terminal groups in the dense star polymer is at least 1.5 times that of a conventional star polymer having similar core and monomeric moieties and a comparable molecular weight and number of core branches wherein each of such branches of the conventional star polymer bears only one terminal group, and (3) a molecular volume that is equal to or less than 80 percent of the molecular volume of said conventional star polymer.

Such covalently bridged dense star polymers are also useful as demulsifiers for oil/water emulsions, wet strength agents in the manufacture of paper, and agents for modifying viscosity in aqueous formulations such as paints.

In certain preferred embodiments, the covalently bridged dense star polymer of the present invention has (1) at least 2 core branches per core, (2) a terminal group density at least 5 times that of the corresponding conventional star polymer, and (3) a molecular volume that is equal to or less than 50 percent of the volume of the conventional star polymer.

In another preferred embodiment, the core of the covalently bridged dense star polymers are derived from a core compound having a plurality of active hydrogens capable of undergoing a Michael's addition reaction with an ethylenically unsaturated group.

In yet another preferred embodiment of the present invention, the covalently bridged dense star polymer of the present invention is a dendrimer covalently bridged to at least one other dendrimer through at least one terminal group of each dendrimer, wherein each dendrimer has a polyvalent core that is covalently bonded to at least 1 ordered dendritic branch which extends to two generations such that each dendritic branch has at least four terminal groups and a symmetrical structure.

In yet another aspect of the present invention are provided processes for preparing the covalently bridged dense star polymers of the present invention. In one embodiment, the covalent bridge is formed by contacting either a dense star polymer or a dendrimer having at least one nucleophilic terminal group with at least one dense star polymer or dendrimer having at least one electrophilic terminal group to form said covalent bridge between said terminal groups.

In another embodiment of the present invention is provided a process for preparing the covalently bridged dense star polymers or dendrimers by contacting a dense star polymer or dendrimer having at least one olefinic terminal group with at least one dense star polymer or dendrimer having a corresponding initiator terminal group to form said covalent bridge between said terminal groups.

In another embodiment of the present invention is provided a process for preparing the covalently bridged dense star polymers or dendrimers. In this process the covalent bridge is formed by contacting a dense star polymer or dendrimer having at least one terminal group which is nucleophilic or olefinic with at least one dendrimer having at least one terminal group which is electrophilic or an initiator, wherein the contacting is performed in the presence of a copolymerizable monomer to form a covalent bridge between said terminal groups of each dense star polymer or dendrimer through said copolymerizable monomer.

In yet another embodiment is provided a process for preparing the covalently bridged dense star polymers of the present invention by heating dense star polymers or dendrimers having nucleophilic, electrophilic, olefinic or initiator terminal groups at temperatures effective to cause covalent bridging among the dense star polymers or dendrimers. Preferably, the dense star polymer or dendrimer has a nucleophilic terminal group, more preferably alkyleneamine groups, derived form ethylenediamine or aziridine moieties.

In yet another embodiment of the present invention, the covalently bridged dense star polymers and dendrimers can be prepared by employing less than the requisite statistical excess of coreactive material needed to prepare a monodispersed (nonbridged) dense star polymer or dendrimer, as described in U.S. Pat. Nos. 4,507,466, 4,558,120 and 4,568,737.

DETAILED DESCRIPTION OF THE ILLUSTRATIVE EMBODIMENTS

The term "substance" is intended to include, in its broadest sense, any composition of matter.

The term "aperture" denotes an opening, a hole, a crater or any fractal surface within or upon a substance.

The term "sub-micron" is intended to refer to apertures in any substances whose diameter is 10,000 Å or less. Substances having sub-micron apertures which can be measured and/or characterized by the process of the present invention include synthetic membranes such as cellulose esters, polysulfones and polypropylene; and natural membranes such as those found in animal cells, plant cells, fungal cells, bacterial cells, protozoan cells, virus particles and other living organisms or from materials derived from organic sources. Other microporous surfaces whose pore sizes can be measured include catalysts such as zeolite, diatomaceous earth and microporous silica.

The term "membrane" denotes a microporous structure, either natural or synthetic, which acts as a filter for substances in the range of molecular dimensions. Membranes generally allow passage of certain ions, water and other solvents, and very small molecules, but are virtually impermeable to larger molecules such as macromolecules (proteins) and colloidal particles.

The most important synthetic membranes are formed from organic polymers. They perform functions that also could be performed by metals, carbon, inorganic glasses, and other materials, but because of their predominant importance in current membrane technology, most synthetic membranes are derived from organic polymers. Early artificial membranes were based on natural polymers such as cellulose, and these still are used. Because of the demand for more versatile and highly tailored membranes, membrane technology currently employs a wide range of other polymeric materials, some synthesized especially for this purpose. The chemical structures of these polymers range from simple hydrocarbons (like polyethylene or polypropylene) to polar structures (like polyamides) or ionic structures in which cations or anions are attached to the backbone.

Microporous membranes are often used as filters. Those with relatively large pores are used in separating coarse, disperse, suspended substances such as particulate contamination in refined sugar, oil pumps, hydraulic oils, etc. Membranes with smaller pores are used for sterile filtration of gases, separation of aerosols, and sterile filtration of pharmaceutical, biological, and heat-sensitive solutions. The very finest membranes can be used to separate or purify soluble macromolecular species.

Membranes also are used in dialysis applications such as removing waste from human blood (hemodialysis), for separation of biopolymers with molecular weights ranging from 10,000 to 100,000, and for analytical measurement of polymer molecular weights. Microporous membranes also may be used as supports for very thin, dense skins or as containers for liquid membranes.

The term "dense star polymer" is a polymer having at least one branch (hereinafter called a core branch) emanating from a core, said branch having at least one terminal group provided that (1) the ratio of terminal groups to the core branches is more than one, preferably two or greater, (2) the density of terminal groups per unit volume in the polymer is at least 1.5 times that of a conventional star polymer having similar core and monomeric moieties and a comparable molecular weight and number of core branches, each of such branches of the conventional star polymer bearing only one terminal group, and (3) a molecular volume that is no more than about 80 percent of the molecular volume of said conventional star polymer as determined by dimensional studies using scaled Corey-Pauling molecular models. The term "dense" as it modifies "star polymer" means that it has a smaller molecular volume than a conventional star polymer having the same molecular weight. The conventional star polymer which is used as the base for comparison with the dense star polymer is one that has the same molecular weight, same core and monomeric components and same number of core branches as the dense star polymer. In addition, while the number of terminal groups is greater for the dense star polymer molecule than in the conventional star polymer molecule, the chemical structure of the terminal groups is the same.

In the dense star polymers, the core is covalently bonded to at least one core branch, preferably at least two, most preferably at least three, core branches with each core branch having a calculated length of at least 3 Angstrom units (Å), preferably at least 4 Å, most preferably at least 6 Å. These polymers preferably have an average of at least 2, more preferably at least 3 and most preferably at least 4 terminal groups per polymer molecule. Preferably, the core branches have a dendritic character, most preferably an ordered dendritic character as defined hereinafter.

The term "bridged dense star polymer" denotes a dense star polymer covalently bridged to at least one other dense star polymer through at least one terminal group of each dense star polymer. Thus, for purposes of this specification, "bridged" and "covalently bridged" can be used interchangeably.

A "dendrimer" is a particular and especially preferred embodiment of the dense star polymer having a polyvalent core that is covalently bonded to at least two ordered dendritic (tree-like) branches which extend through at least two generations (hereinafter exemplified as $D^1$, $D^2$, $D^3$, etc.).

Dendrimers are characterized as having a novel ordered star branched structure (herein called starburst structure).

As an illustration, an ordered second generation dendritic branch is depicted by the following configuration:

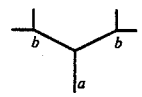

wherein "a" represents the first generation and "b" represents the second generation. An ordered, third generation dendritic branch is depicted by the following configuration:

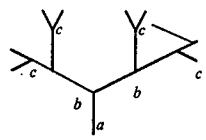

wherein "a" and "b" represent the first and second generation, respectively, and "c" represents the third generation. A primary characteristic of the ordered dendritic branch which distinguishes it from a conventional branch of conventional polymers is the uniform or essentially symmetrical character of the branches as is shown in the foregoing illustrations. In addition, with each new generation, the number of terminal groups on the dendritic branch is an exact multiple of the number of terminal groups in the previous generation.

The term "bridged dendrimer" denotes a dendrimer covalently bridged to at least one other dendrimer through at least one terminal group of each dendrimer as defined hereinbefore.

The term "nucleophilic terminal group" (hereinafter exemplified as NT) means a reactive nucleophilic moiety which serves as a terminal group on a dense star polymer or dendrimer. The contacting of such nucleophilic groups with compatible electrophilic terminal groups result in covalent bridging between the terminal groups.

Representative nucleophilic terminal groups which are suitable for reaction with an electrophilic terminal group include, but are not limited to amino, mercapto, carboxyl, hydroxyl or malonyl acetylenly and acetoacetic acid esters, preferably amino, hydroxyl and mercapto, most preferably amino.

The term "electrophilic terminal group" (hereinafter exemplified as ET) means a reactive electrophilic moiety which serves as a terminal group on a dense star polymer or dendrimer. Such electrophilic groups generally are contacted with compatible nucleophilic terminal groups.

Representative electrophilic groups suitable for reaction with the nucleophilic group include but are not limited to esters, Michael receptor activated olefin, oxirane, aziridinyl, anhydride, allylic, benzylic halide, acid halide, ammonium salt or sulfonium salt, preferably the activated halides and esters.

Where the electrophilic group is a carboxy ester, representative esters include but are not limited to tosylate, mesylate or triflate.

The term "olefinic" terminal group (hereinafter exemplified as OT) means a reactive olefinic moiety which serves as a terminal group on a dense star polymer or dendrimer. Such olefinic terminal groups are attached to the dendrimer through olefin activator groups which make the olefin a polymerizable moiety. These activator include benzyl, arylene, ester, alkylene, alkeamido and ether moieties. Such olefinic terminal groups are of the formula

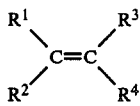

wherein at $R^1$ is an olefinic activator group attached to a dendrimer or dense star polymer as defined above and the remaining $R^2$, $R^3$ and $R^4$ independently represent hydrogen, alkyl, or aryl groups.

Representative olefinic terminal groups which are suitable for reaction with either an initiator or copolymerizable monomer, include but are not limited to acrylate, acrylamido, styryl, methacrylamido, methacrylate, allylic, cinammate or itaconate.

The term "initiator terminal group" (hereinafter exemplified as IT) means a reactive initiator moiety which serves as a terminal group on a dense star polymer or dendrimer. Initiators can be free radicals, cationic, anionic or special ionic centers of what have come to be called Ziegler-Natta, or more broadly, coordination catalysts.

Representative initiator terminal groups include but are not limited to acrylate, acrylamido, styryl, methacrylamido, methacrylate, allylic, cinammate and itaconate.

The term "copolymerizable monomer" (hereinafter exemplified as CM) means any reactive monomer which will react with a dendrimer having at least one terminal group which is nucleophilic or olefinic, with at least one dendrimer having at least one terminal group which is electrophilic or an initiator, wherein said contacting is performed in the presence of a copolymerizable monomer to form a covalent bridge between the terminal group of each dendrimer through said copolymerizable monomer. In this embodiment, the copolymerizable monomer serves as a covalently linked "spacer" between the terminal groups of each dendrimer.

Representative copolymerizable monomers include but are not limited to styrenes, alkylacrylate, alkylmethacrylate, acrylamide, n-alkylamide acylamides, alkenyl oxazolines, vinyl halides, vinylidene halides, itaconates, allylic amines and allylic halides.

The reactivity of the copolymerizable monomer can be determined from copolymerization parameters such as those found in *Polymer Handbook*, Brandrup and Immergut (Ed.) Wiley Interscience, New York, N.Y., 1975.

Process Conditions for Measuring Membrane Pore Size

Methods and materials for conducting separation processes are well known to those skilled in the art. Such processes are taught in H. K. Lonsdale, "The Growth of Membrane Technology" (1982), Journal of Membrane Science, Elsevier Scientific Publishing Company, Amsterdam, Netherlands, Volume 10, pp. 81-181. The preparative teachings of this reference are incorporated herein by reference. Such known processes are also described in "Membrane Technology", D. R. Paul and G. Morel, in the Encyclopedia of Chemical Technology, (1981), John Wiley & Sons, New York, N.Y., Volume 15, pp. 92-131. The preparative teachings of this reference are incorporated herein by reference.

There are three types of separation processes using membranes which are useful for separating particles or ions whose diameter can range between about 10 Å $(0.001\mu)$ to about 10,000 Å $(1.0\mu)$. These three separation processes are known as hyperfiltration (otherwise known as reverse osmosis), ultrafiltration and microfiltration. The chart below provides a summary of the concept of the process, the pore size of the membrane, the materials retained by the membrane, the materials passed through the membrane and the pressures used as the driving force in such separation processes.

| Process | Concept | Range of Pore Size in Membrane | Materials Retained | Materials Passed | Driving Force |
| --- | --- | --- | --- | --- | --- |
| Hyperfiltration (Reverse Osmosis) | Saline Water Feed → Semipermeable Membrane → Concentration / Water | 10–100 Å (0.001–0.01μ) | Virtually all suspended and dissolved salt material | Water | Pressure difference typically 100–800 psi |
| Ultrafiltration | Feed → UF Membrane → Concentration / Water | 20–1000 Å 1000– –1,000,000 daltons | Biologicals such as dextrans and polyglycols, colloids, and macro-molecules. Variable molecular weight cut-offs. | Water and salts | Pressure difference typically 10–100 psi |

| Process | Concept | Range of Pore Size in Membrane | Materials Retained | Materials Passed | Driving Force |
|---|---|---|---|---|---|
| Microfiltration | 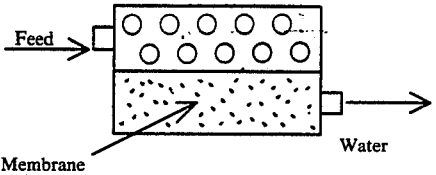 | 1,000–10,000 Å (0.1–1μ) | Suspended material (silica, bacteria, latexes, etc.). Variable particle-size cut-offs. | Water and dissolved species | Pressure difference typically 10 psi |

Hyperfiltration is a process for separating out dissolved salts and other suspended material from saline solutions. Generally, the range of pore sizes in a membrane used in hyperfiltration ranges from about 10–100 Å (0.001–0.01μ). Essentially, the incoming feed (i.e., saline water) is contacted with a semi-permeable membrane. The permeate (i.e., pure water) passes through the semi-permeable membrane while the rejection stream (i.e, concentrated saline solution) remains behind. Of the three processes, hyperfiltration requires the highest pressure to drive the separation, about 100–800 pounds per square inch (psi).

Ultrafiltration is a process for separating out biological materials, colloids and macromolecules from aqueous solutions. Generally, the pore sizes in a membrane used for ultrafiltration range from between about 20–1000 Å (corresponding to molecular weight cut-offs of approximately 1000-one million daltons). Pore sizes of membranes used in ultrafiltration are classified by molecular weight cut-offs, (MWCO). Because there is a pore-size distribution in ultrafiltration membranes, the molecular weight cut-off is never sharp. Essentially, the incoming feed (i.e., aqueous solution of colloids or macromolecules) is contacted with an ultrafiltration membrane. The permeate (i.e., water and salts) passes through the ultrafiltration membrane while the rejection stream (i.e., concentrated colloids and macromolecules) remain behind. Ultrafiltration requires a pressure between that employed in hyperfiltration and microfiltration to drive the separation. Pressures used to drive the separation process in ultrafiltration typically range between about 10 to about 100 psi.

Representative materials used in making ultrafiltration membranes include, but are not limited to, polycarbonate, polyvinyl chloride, polyamides, polysulfone, polyvinylidene fluoride, copolymers of acrylonitrile and vinyl chloride, polyacetal, polyacrylates, polyelectrolyte complexes and cross-linked polyvinyl alcohols.

Microfiltration is a process for separating out suspended material (i.e., silica, bacteria) from solutions. Membranes used in microfiltration have pore size of typically ranging from 1000 to about 10,000 Å or more (0.1–1μ). Essentially, the incoming feed (i.e., suspended silica, bacteriae, latexes) is contacted with a microporous membrane. The permeate (i.e., water and dissolved species) passes through the microporous membrane while the suspended material (i.e, silica, bacteria, latexes) remains behind. Of the three processes, microfiltration requires the lowest pressure to drive the separation. Pressures employed in microfiltration processes typically are about 10 psi or less.

Materials which are used to make microfiltration membranes include, but are not limited to, cellulose nitrate, cellulose acetate, acrylic copolymers, polyvinyl chloride, polyvinylidene fluoride, polyamide and polytetrafluoroethylene.

More recently, in U.S. Pat. Nos. 4,507,466, 4,558,120 and 4,568,737 are described dense star and dendritic polymers which have a dense concentration of functional groups per unit volume of the polymer macromolecule as well as a uniform distribution of such functional groups in the exterior regions of the macromolecule. Loosely stated, a starburst dendrimer has a core from which emanates an exponentially increasing number of dendritic branches. This branching effect causes the resulting dendrimer molecule to be a sterically congested, spherical and non-reptating. By various means, the branching can be carried out in sequential reactions, ensuring monodispersity of the starburst polymer. Such dense star and dendritic polymers have the advantage that they can be dispersed to be soluble in either aqueous or organic solvents. These polymers can also be advantageously designed to be spheroidal and non-reptating. The surface or exterior of such dense star and dendritic polymers can be custom designed to have a cationic (positive), anionic (negative) or neutral charge. By controlling the shape and surface charge, the dense star polymers and dendritic polymers can be made to be more thoroughly monodispersed in a given solvent medium then other structures previously taught.

Also important is the fact that such polymers can be made to have well-defined diameters which can range between about 8 Å–10,000 Å. All of these characteristics of the dense star and dendritic polymers: the solvent solubility, spherical shape, the surface versatility, the monodispersed nature and the well defined dimensions allows them to be a prototype for varying reference dimensions in a systematic fashion so as to permit accurate and precise calibration and characterization of sub-micron apertures.

The sub-micron apertures intrinsic to these and other substances can conveniently be measured by contacting those substances with starburst polymers of known dimensions. The size of the apertures is calculated from measurements of those dense star polymers either passing through or into said aperture, of those starburst polymers or dendrimers not passing through or into the aperture, or of the combined measurements of those starburst polymers passing through or into said apertures and those not passing through. For example, measurements of those starburst polymers or dendrimers passing through or into the membrane could be made by tagging the dense star polymer with a label to trace the activity of the polymer. Such labels include radioactive tags or labels such as Carbon-14, Phosphorous-32, sulfur or iodine and non-radioactive isotopic labels such as Nitrogen-15. Other labels identifying the dense star polymer include fluoroscein. Other types of measurements for determining which size starburst polymers pass through or into the aperture include ultraviolet (UV), visible or fluorescing probes as well.

When the membrane to be characterized is a natural membrane such as that found in a cell, procedures similar to those described hereinabove may be employed. Briefly, the cell surface to be calibrated is contacted by the dense star polymers described hereinbefore. Those polymers passing through the cell membrane are contained within or by the cell. Following separation of the cell from dense star polymers/dendrimers, measurements are made of dense star polymers/dendrimers inside (interior) the cell or those remaining outside (exterior) to the cell to determine the fractions of those sizes which have passed through or into the membrane.

The process for present invention can be used to calibrate the pore size distribution of membranes employed for hyperfiltration (reverse osmosis), ultrafiltration or microfiltration in the following manner. The membrane of choice is contacted with a plurality of dense star polymers whose two-dimensional molecular diameter is known and is in the range from about 8 to about 10,000 Å. Preferably, the range of molecular diameter distributions of the dense star polymer used to calibrate the membrane is fairly narrow. Preferably, the range of variation of molecular diameters of the dense star polymer used to calibrate the membrane is about plus or minus ($\pm$) 5-10 percent, more preferably $\pm$2-5 percent, most preferably less than $\pm$2 percent. The smaller range of variation enables one skilled in the art to more precisely calibrate the pore sizes of the membranes.

After the membrane is contacted with the dense star polymer, those polymers whose 2-dimensional molecular diameters are about equal to or less than the diameter of the aperture of the membrane are passed through or into the apertures of the membrane. Put in analogous terms, the dense star polymer may be thought of as a "ball" similar to a ping pong ball or a basketball and the substance or membrane can be thought of as a "net". The smaller "balls" (the dense star polymers) will pass through or into the bigger holes (the apertures or pores) in the "net" (the membrane). On the other hand, those dense star polymers whose 2-dimensional molecular diameters are greater than the pore sizes of the membrane net will be retained by the membrane and will not pass through the apertures in the membrane. By analogy, the bigger balls (the dense star polymers) will be retained by the smaller holes (the apertures or pores) in the "net" (membrane).

The diameter of the pores or apertures in the membrane can be calculated with information of the size of the dense star polymers either passing through the membrane, not passing through or into and are retained by the membrane, or both. For example, suppose a membrane is contacted with dense star polymers having a range of 2-dimensional diameters ranging from 10-100 Å. Only star polymers being of a diameter of 20 Å or less are found in the solution or permeate passing through the membrane. From this information, the membrane can be said to possess pores whose largest diameter is about 20 Å. Conversely, in the same example, the dense star polymers not passing through and which are retained by the membrane shows dense star polymers are found to range from 20-100 Å. Suppose, however, the 10-20 Å fraction is absent. Such data would also indicate that the upper limit of pore sizes in the membrane is about 20 Å. It will be appreciated that measurements of either (a) those polymers which pass through the membrane or (b) those polymers which do not pass through will yield information on the aperture or pore sizes within the membrane. It will also be appreciated by one skilled in the art that a combination of (a) and (b) will confirm the reliability of measurements of those star polymers passing through or into the aperture with those that do not.

It is known that many substances, including, membranes do not possess a homogeneous or uniformly sized pore size diameter. Rather, many substances contain a range of pore sizes. The method of the present invention can be conveniently adapted to measure and characterize the distribution of the pore diameters in such substances. Separate solutions containing a homogeneously sized dense star polymer are prepared, wherein the separate solutions are organized by polymers decreasing or increasing in size. For example, solutions containing dense star polymers of 10, 20, 30, 40, ... 100 Å are prepared. The solution containing the 10 Å polymer, the smallest size is contacted with the membrane to be calibrated. Measurements of the 10 Å polymer either passing through, retained by the membrane, or both are made as described earlier. The membrane is then contacted with the solution containing the next largest polymer (or smallest depending upon whether the 100 Å polymer solution was used first). Contacting and measurements are continued until nearly all the polymers are retained by the membrane or some acceptable rejection or cut-off percentage is attained. For example, in ultrafiltration procedure, a rejection (equivalent to a retention) of about 90-100 percent can be defined as an acceptable value for determining the molecular weight cut off of a membrane being calibrated. A compilation of these measurements can indicate a pore size distribution of apertures within the membrane.

The following example illustrates the present invention and the manner by which it can be practiced, but as such, should not be construed as limitations upon the overall scope of the same.

EXAMPLE 1

A qualitative comparison of relative pore size distributions between several commercially available porous membranes are made, using the starburst dendrimers. A series of multiple generation starburst dendrimers are from a high purity series prepared and characterized as described in Example 1 in U.S. Pat. No. 4,507,466. Amidoamine synthesis using an ammonia core (I) is employed. The sequence of reactions which can be employed is exhaustive alkylation via Michael addition of methyl acrylate, followed by amidation with ethylenediamine. Each sequence of these reactions leads to the next "generation". The hydrodynamic radii of the series are determined from intrinsic viscosity measurements.

The following membranes are calibrated using the dense star polymers: of a type Amicon YC05-500 molecular weight cutoff (MWCO), from The Amicon Corporation, Lexington, Mass. and types PSA - 1,000 MWCO and PTGC - 10,000 MWCO from Millipore Corporation, Bedford, Mass. The membranes are cut to size and are placed in an Amicon Model 12 UF Module. This module exposes 4 cm$^2$ of membrane area to up to 10 ml of solution under a static head of up to 75 psi. A magnetic stir bar is suspended very close to the membrane surface to reduce gel polarization - the buildup of retained species on the membrane surface, resulting in flux reduction.

The flow rate of deionized water through the membrane can be determined at a convenient pressure (depending on the MWCO). Then, 8 ml of ~5 wt percent starburst solution in deionized water is introduced, and the flow rate and percent solids of the permeate stream are measured periodically. The percent solids in the permeate stream generally does not change over experimental runs. The solids in the initial feed and in the permeate are determined with an American Optical Model 10440 hand-held refractometer, American Optical Corporation, Southbridge, Mass. The experiment can be carried out for a length of time sufficient to collect 4-5 ml of permeate. The percent retention by the membranes of the dendrimer can be determined as A percent retention (% R) of 100 means that none of the dendrimer in the C-feed has passed through the membrane.

A percent retention of 0 (zero) means that all or 100 percent of the dendrimer in the C-feed has passed through the membrane.

The accuracy of the percent retention is poor at the two extremes (0 and 100 percent) since the refractometer precision is low.

Table 1 shows the results including applied pressure, flow rates, and retention. Also given is an indication of gel polarization. This is observed as a decrease in solution flux with time. The percent reduction of flux due to this effect is derived from the difference between the initial and final flow rates. In those cases where gel polarization is observed, the total time weighted average flux is used to determine the percent flux reduction as compared to deionized water.

TABLE 1

STARBURST RETENTION ON VARIOUS UF MEMBRANES

| Membrane | Starburst Generation | Dendrimer Diameter (Å) | Pressure psi | Deionized Water Flow (ml/min) | Flow of Starburst Containing Solution (ml/min) | % Flux Reduction | % Retention of the Starburst Dendrimer by the membrane | Gel Polarization[a] |
|---|---|---|---|---|---|---|---|---|
| Amicon YCO5 | 1 | 11 | 40 | .11 | .012 | 89 | 60 | — |
| 500 MWCO | 3 | 23 | 40 | .09 | .010 | 89 | 79 | 42 |
|  | 4 | 31 | 40 | .07 | .037 | 47 | 94 | 29 |
|  | 5 | 49 | 40 | .08 | .042 | 48 | 99 | — |
| Millipore | 1 | 11 | 40 | .11 | .013 | 88 | 55 | — |
| PSA | 3 | 23 | 40 | .13 | .018 | 86 | 74 | 23 |
| 1,000 MWCO | 4 | 31 | 40 | .12 | .037 | 69 | 93 | 17 |
|  | 5 | 49 | 40 | .12 | .035 | 71 | 98 | — |
| Millipore | 1 | 11 | 20 | .80 | .54 | 33 | 9 | — |
| PTGC | 3 | 23 | 10 | .64 | .17 | 74 | 24 | — |
| 10,000 MWCO | 4 | 31 | 10 | .60 | .17 | 72 | 43 | — |
|  | 5 | 49 | 10 | .53 | .11 | 80 | 69 | 25 |

[a]Percent Reduction in the Solution Flux Due to Gel Polarization $$\% R = \left[1 - \frac{C\ \text{permeate}}{C\ \text{feed}}\right] \times 100$$

where
% R = percent of dendrimer retained on the membrane
C permeate = concentration of dendrimer in the permeate solution passing through the membrane and
C feed = concentration of dendrimer in solution applied to the membrane surface.

Preparation of Bridged Dense Star Polymers and Dendrimers

The covalently-bridged dense star polymers of the present invention can be prepared by any suitable method. Such suitable methods include reactions of condensation, addition utilizing a radical mechanism and addition utilizing an ionic mechanism as described in *Preparative Methods of Polymer Chemistry*, 2nd Edition, W. R. Sorenson and T. W. Campbell, Interscience Publishers, New York (1968); whose preparative teachings are incorporated herein by reference.

Various methods are schematically illustrated in Table 2 for preparing the covalently bridged dense star polymers or dendrimers of the present invention.

TABLE 2

| PREPARATION NUMBER | REACTION MECHANISM | DENSE STAR POLYMER PRODUCT | |
|---|---|---|---|
| 1 | 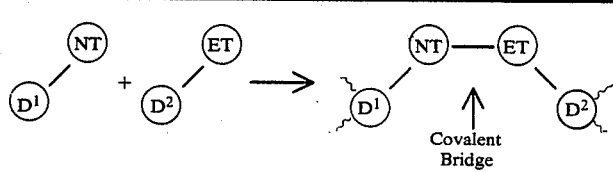 | | (I) |

TABLE 2-continued

| PREPARATION NUMBER | REACTION MECHANISM | DENSE STAR POLYMER PRODUCT | |
|---|---|---|---|
| 2 | (NT)−D¹ + (ET)−D² + $E_{n1}RE_{n2}$ ⟶ | (NT)−$E_{n1}RE_{n2}$−(NT), D¹ ... D² | (II) |
| 3 | (NT)−D¹ + (ET)(ET)−D³ + (NT)−D² ⟶ | (NT)−(ET)(ET)−(NT), D¹ D³ D² | (III) |
| 4 | (ET)−D¹ + (ET)−D² + $N_{n1}^{1}RN_{n2}^{2}$ ⟶ | (ET)−$N_{n1}^{1}N_{n2}^{2}$−(ET), D¹ ↑R D² | (IV) |
| 5 | (ET)(NT)−D¹ + (NT)(ET)−D³ + −D² ⟶ | (ET)−(NT)(NT)−(ET), D¹ D³ + D² | (V) |
| 6 | (OT)−D¹ + (IT)−D² ⟶ | (OT)−(IT), D¹ D² | (VI) |
| 7 | (OT)−D¹ + [CM] + (IT)−D² ⟶ | (OT)−[CM]−(CT), D¹ D² | (VII) |

Referring to Table 2, in Preparation No. 1, a condensation reaction, dendrimer ($D^1$) having at least one nucleophilic terminal group (NT) is contacted with a second dendrimer ($D^2$) having one electrophilic terminal group (ET) to yield a covalently bridged dense star polymer or dendrimer product of Formula (I). For example, an amine terminated dendrimer can be reacted with an ester terminated dendrimer to covalently bridge the two dendrimers through a covalent amide bridge. Similarly, the wavy lines (∼) connected to dendrimers $D^1$ and $D^2$ indicated that bridged dendrimers of Formula (I) can be further polymerized with other dendrimers, forming even larger bridged dense star polymers or dendrimers.

EXAMPLE 2.

Reaction of Dendrimer A (Generation=2.5 ($NH_3$ Core)) With Dendrimer B (Generation=3.0 ($NH_3$ Core))

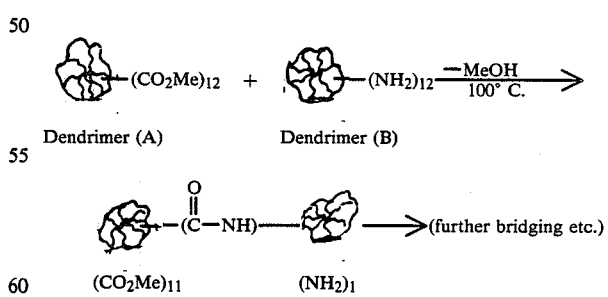

Into a vial is charged Dendrimer (A), molecular weight (MW) 2,804, (0.28 (grams) g) and Dendrimer (B), MW 3,252, (0.32 g), to give a colloidal, opaque paste. Adding 2 ml of deuterated chloroform ($CDCl_3$) causes a portion of the dendrimer mixture to dissolve. Adding ≃0.5 ml of MeOH obtains a totally homogeneous solution. A film (≃1 ml) of this reaction mixture is cast on (a) an infrared salt plate and (b) on Teflon ® coated plate. Teflon ® is a trademark of the Du Pont de Nemours Co., Wilmington, Del. 19898. These samples are placed in an oven at 100° C. and are monitored by infrared analysis over a period of 65 hours (hr). Ratios of ester (1730 cm$^{-1}$ to amide (1652 cm$^{-1}$) bands are determined and are as shown in Table 3.

TABLE 3

| Time Elapsed (Hours) | % Ester (1730 cm$^{-1}$) | % Amide (1652 cm$^{-1}$) |
|---|---|---|
| 0.00 | 42% | 57% |
| 0.83 | 39% | 61% |
| 21.00 | 32% | 68% |
| 30.50 | 30% | 70% |
| 47.00 | 27% | 73% |
| 65.00 | 23% | 77% |

The ester band (1730 cm$^{-1}$) diminishes dramatically (≅10 percent; ≅0.5 percent/hr) during the first 21 hrs (100°) with concurrent formation of amide band (1652 cm$^{-1}$). After that time, loss of ester levels out at ≅0.2 percent/hr and continues at that rate after 65 hrs/100°. The film is removed from the TFE plate after 30 hrs, dissolved/slurried in water and filtered through an XM-300 (≅200 Å±; MWCO ≅300,00, cut-off) obtained from Amicon Corporation, Lexington, Mass. The filterate is re-filtered through an XM-100 (≅Å): MWCO ≅100,000 cut-off) and the retained sample portion is diluted with H$_2$O and examined by electron microscopy. Us the method of Richardson and Quayle the sample is sprayed on a carbon coated (50 Å), beryllium grid and examined by a Philips 400 TEM microscope. Electron micrographs show the major population is made of "starburst polymer" aggregates with cross-sectional dimensions of ≅50–600 Å.

In Preparation No. 2, dendrimers having a nucleophilic terminal group are contacted with electrophilic reagent $En_1^1REn_2^2$, defined hereinbelow, to yield a dense star polymer product or bridged dendrimer of Formula (II).

The electrophilic reagent is defined as $En_1^1REn_2^2$ wherein $E^1$ and $E^2$ independently represent electrophilic groups as defined hereinbefore;

$n_1$ and $n_2$ independently represent integers from 1 to 10; and

R represents arylene and alkylene moieties.

Bridged dendrimers of Formula (II) can be polymerized with other dendrimers to form even larger bridged dense star polymers or dendrimers.

In Preparation No. 3, dendrimers $D^1$ and $D^2$ having terminal nucleophilic groups can be contacted with a third dendrimer $D^3$ having electrophilic terminal groups, to yield a bridged dense star polymer or bridged dendrimer of Formula III. The bridged dendrimers of Formula III can be polymerized further to yield even larger bridged dense star polymers or dendrimers.

In Preparation No. 4, a condensation reaction, dendrimers having electrophilic terminal groups can be contacted with a nucleophilic reagent $N_{n1}^1RN_{n2}^2$ to yield dense star polymer or bridged dendrimer of Formula (IV). The nucleophilic reagent is defined as $N_{n1}^1RN_{n2}^2$ wherein $N^1$ and $N^2$ independently represent nucleophilic groups as defined hereinbefore;

$n_1$ and $n_2$ independently represent integers from 1 to 10; and

R represents arylene and alkylene moieties.

For example, an amine terminated dendrimer can be contacted with di- or multi-substituted benzyl halides to covalently bridge the dendrimers. The bridged dendrimer of Formula (IV) can be polymerized further to yield even larger covalently bridged dense star polymers or dendrimers.

In Preparation No. 5, dendrimers $D^1$ and $D^2$ having electrophilic terminal groups are contacted with a third dendrimer $D^3$ having nucleophilic terminal groups to yield a bridged dense star polymer or dendrimer of Formula (V). For example, dendrimers having ester terminated groups can be contacted with di- or multi-substituted polyamines or polyols to covalently bridge the dendrimers. The bridged dendrimer of Formula (V) can be polymerized further to yield even larger bridged dense star polymers or dendrimers.

In Preparation No. 6, a dendrimer having at least one olefinic terminal group (OT) is contacted with a second dendrimer having at least one initiator (IT) (copolymerizable) terminal group to yield a bridged dense star polymer or dendrimer of Formula (VI). The bridged dense star polymer or dendrimer of Formula (VI) can be polymerized further to yield even larger bridged dense star polymers or dendrimers.

In Preparation No. 7, a dendrimer having an olefinic terminal group and dendrimer having a initiator (IT) (copolymerizable) terminal group are contacted with a copolymerizable monomer to form a bridged dense star polymer or dendrimer of Formula (VII). The bridged dendrimer of Formula (VII) can be polymerized further to yield even larger bridged dense star polymers.

In Preparation No. 8 dense star polymers having nucleophilic, electrophilic, olefinic or initiator terminal groups can be heated to temperatures effective to effect covalent bridging among the dense star polymers or dendrimers. For example, heating amine terminated polyamidoamines (PAMAM) dendrimers at temperatures between about 150°–200° C. for an effective time will transaminate the amine terminal groups, forming the covalent bridging between dendrimers. A representative example of this preparation is provided below.

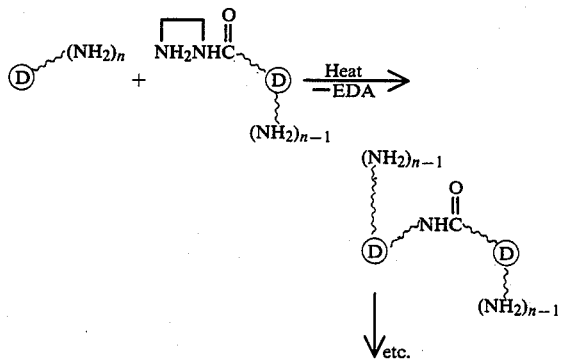

In Preparation No. 9 the covalently bridged dense star polymers or dendrimers can be prepared by employing less than the statistical excess of a coreactant such as ethylenediamine (EDA) used in preparing the monodispersed (nonbridged) dense star or dendrimer.

EXAMPLE 3

Monodispersed dendrimers 0.5 Generation from an ammonia (NH$_3$) core were prepared by exhaustive alkylation (Michael addition) of ammonia with methyl acrylate. The monodispersed dendrimers were contacted with ethylenediamine (EDA) in a series of molar ratios ranging from 10:1 to 2:1 (EDA:dendrimer).

The reaction product from each contacting is vacuum stripped of excess ethylenediamine and methanol, the by-product of the reaction. The products were then analyzed by size exclusion chromatography using Spherogel® TSK 2000 and 3000 PW columns available from Beckman Instruments, Inc., Berkeley, Calif. The columns were connected in series and each was 30 cm in length. The eluent was 0.05 M $K_2HPO_4$ pH adjusted to 11 with 50 weight percent NaOH. Injections were 0.1 ml of 0.5 percent solution and the flow rate was 1 ml/min. Differential refractive index detection was used to monitor the dense star polymer elution. This chromatographic method was capable of resolving the first generation dendrimer from the various bridged dendrimer species which elute earlier. Table 4 shows the purity of the product from each contacting expressed as weight percent first generation dendrimer in the product.

TABLE 4

| Mole Ratio EDA:0.5 G Dendrimer | Weight Percent 1 G Dendrimer in Product |
| --- | --- |
| 10:1 | 76 |
| 7:1 | 62 |
| 5:1 | 44 |
| 3:1 | 19 |
| 2:1 | Sample Gelled |

Table 4 clearly shows that this process yields a smaller and smaller portion of the desired product as the ratio of EDA to the starting dendrimer is decreased. Furthermore, the chromatograms show that as this ratio is decreased, the product contains bridged dendrimer of higher and higher molecular weight until at the 2:1 ratio the product is a gel.

The covalently bridged dense star polymers and the bridged dendrimers of the present invention are prepared under conditions similar to those used in preparing the dense star polymers, as taught in U.S. Pat. Nos. 4,558,120, 4,568,737 and 4,507,466 whose preparative teachings are incorporated herein by reference. Dense star polymers or dendrimer starting materials having the requisite reactive nucleophilic, electrophilic, olefinic or initiator terminal groups can be contacted at temperatures ranging from −10° C. to about 250° C., preferably from ambient to about 150° C. The dense star polymers or dendrimer starting materials can be contacted at autogenous pressures, although pressures less than or greater than autogenous can be employed. The dense star polymers or dendrimer starting materials can be stirred or not stirred during the contacting, although stirring is preferred. The resultant covalently bridged dense star polymers or dendrimers can be recovered after covalent bridging of the dense star polymer or dendrimer starting materials by conventional procedures, such as solvent extraction, crystallization, precipitation, evaporation, and filtration. The molar ratios of dense star polymer or dendrimer starting materials can vary greatly, depending upon the degree of covalent bridging desired, the desired geometric configuration of the bridged dense star polymer or dendrimer, and the desired degree of activity of the residual terminal groups on the bridged dense star polymer or dendrimer. The requisite molar ratio of reactants can be established by one of ordinary skill.

In addition to the simplified situation where only two dense star polymers or dendrimers starting materials are covalently bridged, multiple dense star polymer or dendrimer can be bridged, i.e., polymerized together to form bridged dense star polymers or dendrimers of a multitudinous variety of shapes and sizes.

The following diagram represents a bridged dense star polymer or dendrimer whose dense star polymers or dendrimers are covalently bridged linearly. For purposes of illustration, each circle represents a dendrimer specie and the lines connecting the circles represent the covalent bridges between the dendrimers.

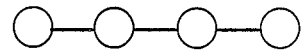

In the diagram below, the bridged dense star polymer or dendrimer whose dense star polymers or dendrimers are covalently bridged in a "starburst" or radially expanding manner.

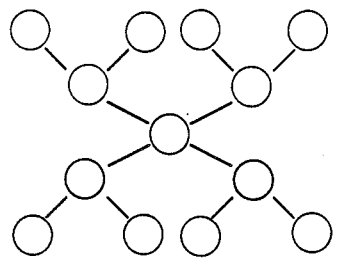

Such bridged dense star polymers and dendrimers can also be made from dense star polymers and dendrimers covalently bridged in a concentric or macrocyclic manner:

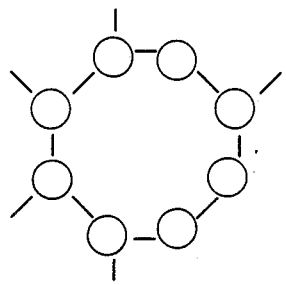

Such bridged dense star polymers or dendrimers can also be made from dense star polymers and dendrimers covalently bridged in rod-like structures:

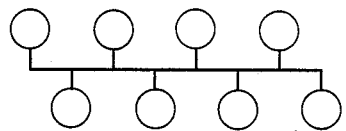

A dense star polymer or dendrimer "seed" possessing electrophilic terminal groups i.e., esters as described in Preparation No. 3, supra, can be contacted with a plurality or excess of dense star polymers or dendrimers possessing nucleophilic terminal groups, i.e., amines. The excess dendrimers with nucleophilic terminal groups "coat" the dense star or dendrimer "seed", analogous to rolling a candy or pastry (seed) in flour (coreactant coating). For example, if the seed has electrophilic terminal groups, the coating will have nucleophilic terminal groups. Conversely, if the seed has nucleophilic terminal groups, the coating will have electrophilic terminal groups. See, for example, Preparation No. 5. Such an enhanced bridged dense star polymer or dendrimer is illustrated as follows.

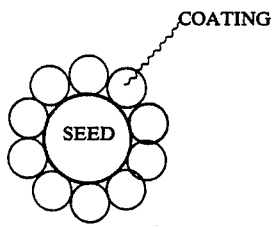

Dense star polymers whose dendrimers are covalently bridged can advantageously be constructed to possess cavitations or voids in highly bridged aggregates.

These bridged aggregates or lattices can still retain further reactivity through reactive terminal groups not used in the bridging. In addition, these dendrimer bridging reactions can be performed as to yield films, gels, beads or other fabricated shapes which possess cavitations or voids which are based on the "packing efficiency" of the dense star polymers and dendrimers being covalently bridged.

The block diagrams below schematically illustrate how the cavity size and shapes can be designed based on the covalent bridging of selected dendrimers.

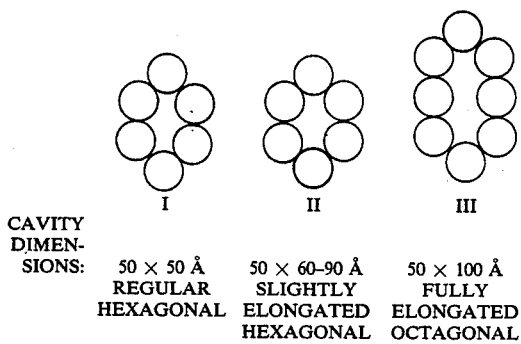

| | I | II | III |
|---|---|---|---|
| CAVITY DIMENSIONS: | 50 × 50 Å REGULAR HEXAGONAL | 50 × 60–90 Å SLIGHTLY ELONGATED HEXAGONAL | 50 × 100 Å FULLY ELONGATED OCTAGONAL |

The cavity sizes can be controlled to a large degree by the choice of dendrimer size employed. Bridging dense star polymers and dendrimers having large diameters will lead to aggregates having a correspondingly large cavity sizes. Conversely, bridging dense star polymers and dendrimers having small diameters will result in aggregates having small cavity sizes. For example, based on (CPK) dimensions for various $NH_3$ core derived dendrimers and assuming the dendrimers will hexagonally pack (see Table 1), bridged dendrimer aggregates having cavity sizes ranging from Generation=1.0 (22×22–44Å) to Generation=7.0 (126×126–252Å) can be prepared.

These cavity dimensions combined with various organic moieties can serve as size selective lattices/matrices for physical separation of, modification of and catalysis reactions of a wide variety of valuable bioparticles possessing microdimensions similar to these cavities.

Preparation of Starting Materials

Methods are known for preparing dense star polymers and dendrimers having nucleophilic, electrophilic, olefinic or initiator terminal groups as taught in U.S. Pat. Nos. 4,507,466, 4,558,120 and 4,568,737 whose preparative teachings are incorporated herein by reference.

Suitable nucleophilic, electrophilic, olefinic or initiator groups are known to those skilled in the art. See, for example, *Preparative Methods of Polymer Chemistry supra*.

For the purposes of this specification, a two-dimensional molecular diameter is determined by the electron microscopic method described in U.S. Pat. Nos. 4,568,737, 4,558,120 and 4,507,466.

The dense star polyamines can have two-dimensional molecular diameters in the range from about 6 to about 1000, more preferably from about 10 to about 250, most preferably from about 25 to about 125, Angstrom units. For the purposes of this specification, a three-dimensional molecular diameter is determined by calculating hydrodynamic diameters using the following Hester-Mitchell relationship, R. D. Hester et al., *J. Poly Sci.*, Vol. 18, p. 1727 (1980).

$$d = \left[ \frac{240}{\pi N} \right]^{\frac{1}{3}} [M(\eta)]^{\frac{1}{3}} \times 10^8$$

wherein d is the hydrodynamic diameter in Angstrom units; N is $6.02 \times 10^{23}$; M is number average molecular weight of the dendrimer; $\pi$ is 3.14; and $\eta$ is intrinsic viscosity of the dense star polyamine in deciliters per gram at 25° C.

In dense star polyamines, the terminal groups are amino groups, preferably primary amino groups. While less preferred for many applications, the amino groups may be secondary amino, e.g., methylamino, ethylamino, hydroxyethylamino, benzylamino or mercaptoethylamino; or tertiary amino, e.g., dimethylamino, diethylamino, bis(hydroxyethyl)amino, or other N-alkylated, N-arylated or N-acylated derivatives obtained by reaction with various alkylating agents, arylating agents or acylating agents, respectively. It is further understood that the terminal amino groups of the dense star polyamines may be substituted with other groups using conventional procedures as described in detail hereinafter. The dense star polyamines differ from conventional star or star-branched polyamines in that the dense star polyamines have a greater concentration of terminal groups per unit of molecular volume than do extended conventional star polyamines having an equivalent number of core branches and an equivalent core branch weight. Thus, the density of terminal amino groups per unit volume in the dense star polyamine is at least about 1.5 times the density of terminal groups in the extended conventional star polyamine, preferably at least 5 times, more preferably at least 10 times, most preferably from about 15 to about 50 times. The ratio of terminal groups per core branch in the dense star polyamine is preferably at least 2, more preferably at least 3, most preferably from about 4 to about 1024. Preferably, for a given polyamine molecular weight, the molecular volume of the dense star polyamine is less than 70 volume percent, more preferably from about 16 to about 60, most preferably from about 7 to about 50 volume percent of the molecular volume of the extended conventional star polyamine.

In the preferred dense star polyamines, the density of terminal primary amine moieties in the polyamine is readily expressed as the molar ratio of primary amine moieties to the total of secondary and tertiary amine moieties. In such polymers this 1° amine: (2° amino +3° amine) is preferably from about 0.37:1 to about 1.33:1, more preferably from about 0.69:1 to about 1.2:1, most prefperably from about 1.0:1 to about 1.2:1.

The preferred dendrimers of the present invention are characterized as having a polyvalent core that is covalently bonded to at least two ordered dendritic branches which extend through at least two generations. Such ordered branching can be illustrated by the following sequence wherein G indicates the number of generations:

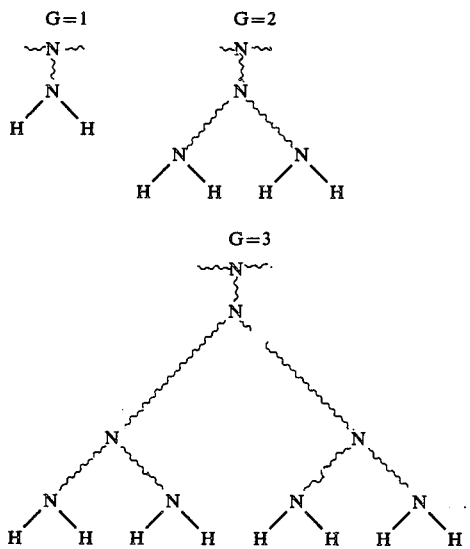

Mathematically, the relationship between the number of terminal groups on a dendritic branch and the number of generations of the branch in a homopolymer dendrimer can be represented as follows:

$$\text{\# of terminal groups per dendritic branch} = \frac{N_r{}^G}{2}$$

wherein G is the number of generations and $N_r$ is the repeating unit multiplicity which is at least 2 as in the case of amines. The total number of terminal groups in the dendrimer is determined by the following:

$$\text{\# of terminal groups per dendrimer} = \frac{N_c N_r{}^G}{2}$$

wherein G and $N_r$ are as defined before and $N_c$ represents the valency (often called core functionality) of the core compound. Accordingly, the homopolymer dendrimers of the present invention can be represented in its component parts as follows:

$$\left[ (\text{Core}) \left[ (\text{Repeat Unit}) \frac{N_r{}^G - 1}{N_r - 1} \text{Terminal Moiety} \frac{N_r{}^G}{2} \right] \right] N_c$$

wherein the Core, Terminal Moiety, G and $N_c$ are as defined before and the Repeat Unit has a valency or functionality of $N_r+1$ wherein $N_r$ is as defined before.

A copolymer dendrimer which is preferred for the purposes of this invention is a unique compound constructed of polyfunctional monomer units in a highly branched (dendritic) array. The dendrimer molecule is prepared from a polyfunctional initiator unit (core compound), polyfunctional repeating units and terminal units which may be the same or different from the repeating units. The core compound is represented by the formula $\text{(I)}(Z^c)_{Nc}$ wherein $\text{(I)}$ represents the core, Z represents the functional groups bonded to $\text{(I)}$ and $N_c$ represents the core functionality which is preferably 2 or more, most preferably 3 or more. Thus, the dendrimer molecule comprises a polyfunctional core, $\text{(I)}$, bonded to a number ($N_c$) of functional groups, $Z^c$, of which is connected to the monofunctional tail of a repeating unit, $X^1Y^1(Z^1)_{N1}$, of the first generation and each of the Z groups of the repeating unit of one generation is bonded to a monofunctional tail of a repeating unit of the next generation until the terminal generation is reached. In the dendrimer molecule, the repeating units are the same within a single generation, but may differ from generation to generation. In the repeating unit, $X^1Y^1(Z^1)_{N1}$, $X^1$ represents the monofunctional tail of the first generation repeating unit, $Y^1$ represents the moiety constituting the first generation, $Z^1$ represents the functional group of the polyfunctional head of the repeating unit of the first generation and may be the same as or different from the functional groups of the core compound $\text{(I)}(Z)_{Nc}$, or other generations; and $N^1$ is a number of 2 or more, most preferably 2, 3 or 4, which represents the multiplicity of the polyfunctional head of the repeating unit in the first generation. Generically, the repeating unit is represented by the formula $X^i Y^i (Z^i)_{Ni}$ wherein "i" represents the particular generation from the first to the t-1 generation. Thus, in the preferred dendrimer molecule, each $Z^1$ of the first generation repeating unit is connected to an $X^2$ of a repeating unit of the second generation and so on through the generations such that each $Z^i$ group for a repeating unit $X^i Y^i (Z^i)_{Ni}$ in generation number "i" is connected to the tail ($X^{i+1}$) of the repeating unit of the generation number "i+1". The final or terminal generation of a preferred dendrimer molecule comprises terminal units, $X^t Y^t (Z^t)_{Nt}$ wherein t represents terminal generation and corresponds to the total number of generations and $X^t$, $Y^t$, $Z^t$ and $N^t$ may be the same as or different from $X^i$, $Y^i$, $Z^i$ and $N^i$ except that there is no succeeding generation connected to the $Z^t$ groups and $N^t$ may be less than two, e.g., zero or one. Therefore the preferred dendrimer has a molecular formula represented by $$I(Z^c)_{Nc}\left[ (X^i Y^i(Z^i)_{Ni})N_c \prod_{n=1}^{i-1} N^n \right] (X^t Y^t(Z^t)_{Nt})N_c \pi N^n.$$

for $i = 0$ to $t - 1$ wherein the symbols are as previously defined. The $\pi$ function is the product of all the values between its defined limits. Thus $$\prod_{n=1}^{i-1} N^n = (N^1)(N^2)(N^3)(N^{i-2})(N^{i-1})$$

which is the number of repeat units, $X^iY^i(Z^i)_{Ni}$, comprising the ith generation of one dendritic branch. In copolymer dendrimers, the repeat unit for one generation differs from the repeat unit in at least one other generation. The preferred dendrimers are very symmetrical as illustrated in structural formulas described hereinafter. Preferred dendrimers may be converted to functionalized dendrimers by contact with another reagent. For example, conversion of primary amines in the terminal generation to amides by reaction with an acid chloride gives an amide terminally functionalized dendrimer. Quaternization of the internal tertiary amines by contact with dimethyl sulfate gives a quaternary ammonium internally functionalized dendrimers. The dendrimers may be functionalized terminally, internally, or both. This functionalization need not be carried out to the theoretical maximum as defined by the number of available functional groups and, thus, a functionalized dendrimer may not have high symmetry or a precisely defined molecular formula as is the case with the present dendrimer.

An illustration of a functionally active dendrimer of a ternary or trivalent core which has three ordered, second generation dendritic branches is depicted by the following configuration:

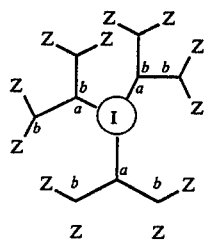

wherein "I" is a trivalent core atom or molecule having a covalent bond with each of the three dendritic branches, "Z" is a terminal amine moiety and "a" and "b" are as defined hereinbefore. An example of such a ternary dendrimer is polyamine represented by the following structural formula:

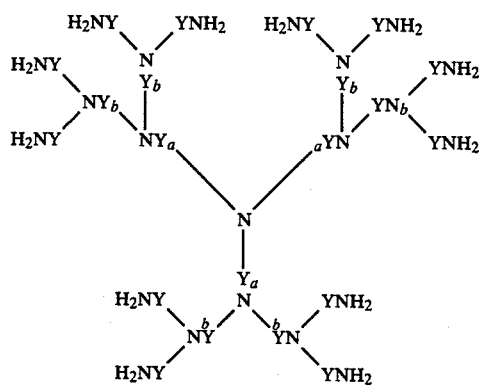

wherein Y represents a divalent alkylene moiety such as ethylene ($-CH_2CH_2-$), propylene ($-CH_2CH_2CH_2-$ or $-CH_2CHCH_3$) and other alkylenes having from 4 to 6 carbons and alkyleneamino, alkyleneaminoalkylene and polyalkylenepolyamine, and "a" and "b" indicate first and second generations, respectively. In these two illustrations, $N_c$ is 3 and $N_r$ is 2. In the latter of the two illustrations, the Repeat Unit is YN. While the foregoing configuration and formula illustrate a trivalent core, the core atom or molecule may be any monovalent or monofunctional moiety or any polyvalent or polyfunctional moiety, preferably a polyvalent or polyfunctional moiety having from 2 to about 2300 valence bonds or functional sites available for bonding with the dendritic branches, most preferably from about 3 to about 200 valence bonds or functional sites. In cases wherein the core is a monovalent or monofunctional moiety, the dense star polyamine has only one core branch and must be compared with a linear polyamine in order to determine appropriate terminal group density and molecular volume. Accordingly, this dense star polyamine must have at least 2 generations in order to exhibit the desired density of terminal groups. Also, Y may be any other divalent organic moiety such as arylene (e.g., phenylene), arylenealkylene, alkylenearylenealkylene, alkyleneoxy (e.g., ethyleneoxy), and the like, with the depicted alkylene moiety being more preferred and ethylene being the most preferred. It is further understood that Y may be a polyvalent moiety such as triyls, tetrayls and other polyyls of aliphatic and aromatic hydrocarbons, e.g.,

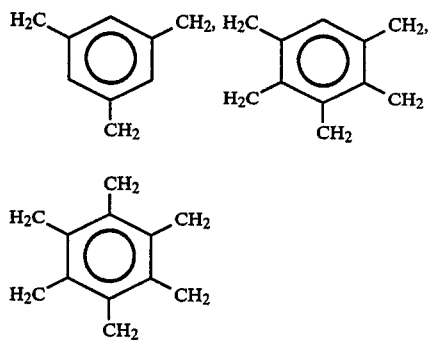

and the like. In addition to amine, the terminal groups of the dendrimer may be any functionally active moiety that can be used to propagate the dendritic branch to the next generation. Examples of such other moieties include ester moieties such as alkoxycarbonyl, ethylenically unsaturated moieties such as alkenyl, aziridinyl, oxazolinyl, haloalkyl, oxiranyl, mercapto, hydroxy, isothiocyanato and isocyanato, with amino moieties being preferred. While the dendrimers preferably comprise dendritic branches having 2 to 6 generations, dendrimers comprising dendritic branches up to 12 generations are suitably made and employed in the practice of this invention.

More preferably, the amine dendrimers of this invention are represented by the formula:

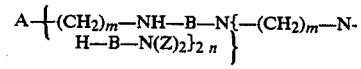

wherein A is an n-valent core derived from ammonia or an amine compound, B is a divalent moiety capable of linking amine groups, m is an integer of 2 to 12, n is an integer of 3 or more corresponding to the number of the core branches and Z is hydrogen, alkyl aryl, alkylaryl, hydroxyalkyl, mercaptoalkyl, alkoxycarbonyl,

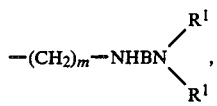

wherein $R^1$ is hydrogen or

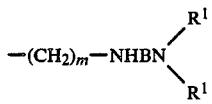

wherein each generation is represented by

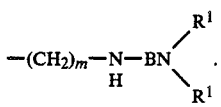

More preferably A is a core such as

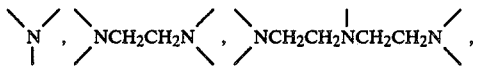

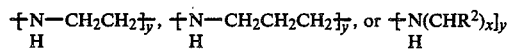

wherein $R^2$ is alkyl or aryl, x is 2 or 3 and y is an integer from 2 to 2300; B is the divalent residue of a polyamine, most preferably an alkylene polyamine such as ethylene diamine or a polyalkylene polyamine such as triethylene tetramine; n is an integer from 3 to 2000, more preferably from 3 to 1000, most preferably from 3 to 125; m is 2 to 12, preferably 2 to 6; and Z is most preferably

wherein $R^2$ is alkyl,

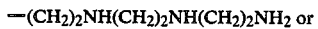

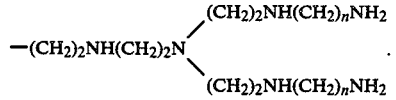

The dense star polyamines of this invention are readily prepared by reacting a compound capable of generating a polyvalent core with a compound or compounds which causes propagation of dendritic branches from the core. The compound capable of generating a polyvalent core, $W(X)_n$, wherein W is the polyvalent core atom and is covalently bonded to nX reactive terminal groups (usually amino and $n \geq 2$), is reacted with a partially protected multifunctional reagent, T—U(V)$_y$, wherein U represents a multivalent moiety covalently bonded to y(V) protected moieties ($y \geq 2$), and to one T, a moiety capable of reacting with X to form $W[(X'—T'-\!\!+\!\!U(V)_y]_n$, wherein X' and T' represent the residue of reaction between X and T. This first generation compound is then subjected to activation conditions whereby are made reactive (V) moieties are made reactive (deprotected) and reacted with the partially protected multifunctional reagent, T—U—(V)$_y$, to form the second generation protected dendrimer, $W[(X'—T'-\!\!+\!\!U(V)_y T'—U(V)_y]_n$. This protected dendrimer can be activated and reacted again in a similar manner to provide the third generation protected dendrimer. This partially protected reactant method is specifically illustrated hereinafter.

Illustrative of the partially protected reactant method, dense star polyamines including polyamine dendrimers may be prepared by reacting ammonia or an amine having a plurality of primary amine groups with N-substituted aziridine such as N-tosyl aziridine,

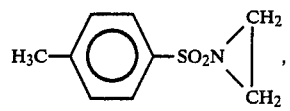

N-methanesulfonyl aziridine, N-trifluoromethanesulfonyl aziridine; N-acyl aziridines such as

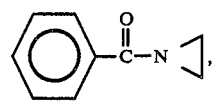

and the corresponding azetidine derivatives, e.g.,

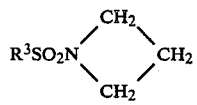

wherein $R^3$ is alkyl such as methyl, ethyl and propyl; aryl such as phenyl; and polyfluoroalkyl such as trifluoromethyl or other perfluoroalkyl, to form a protected first generation polysulfonamide. This product is then activated with acid such as hydrochloric or sulfuric acid to form the first generation polyamine salt, neutralized with sodium hydroxide and then reacted with further N-tosyl aziridine to form the protected second generation polysulfonamide which sequence can be repeated to produce higher generation polyamines using the general reaction conditions described in Humrichause, C. P., PhD, Thesis from University of Pennsylvania, "N-Substituted Aziridines as Alkylating Agents", Ref. No. 66-10, 624 (1966).

In the foregoing method of dense star polyamine preparation, water or hydrogen sulfide may be employed as nucleophilic cores for the production of binary dendrimers. Examples of other nucleophilic core compounds include phosphine, polyalkylene polyamines such as diethylenetriamine, triethylenetetramine, tetraethylenepentamine and both linear and branched polyethylenimine; primary amines such as methylamine, hydroxyethylamine, octadecylamine and polymethylenediamines such as hexamethylenediamine; polyaminoalkylarenes such as 1,3,5-tris(aminomethyl)-benzene; tris(aminoalkyl)amines such as tris(aminoethyl)amine; heterocyclic amines such as imidazolines and piperidines; and various other amines such as hydroxyethylaminoethylamine, mercaptoethylamine, morpholine, piperazine, amino derivatives of polyvinylbenzyl chloride and other benzylic polyamines such as tris(1,3,5-aminomethyl)benzene. Other suitable nucleophilic cores include polyols such as the aforementioned pentaerythritol, ethylene glycol and polyalkylene polyols such as polyethylene glycol and polypropylene glycol; 1,2-dimercaptoethane and polyalkylene polymercaptans; thiophenols, and phenols. Of the core compounds, ammonia, alkylene diamines and the polyalkylene polyamines are preferred for the preparation of polyamine dendrimers and other dense star polyamines by this method. Also preferred as core compounds are the star/comb-branched polyamines described in U.S. patent application Ser. No. 683,299, filed Dec. 14, 1984, and now U.S. Pat. No. 4,599,400 which is hereby incorporated by reference in its entirety.

Examples of N-substituted aziridines suitably employed in this invention include N-tosyl aziridine, N-methanesulfonyl aziridine, N-trifluoromethanesulfonyl aziridine, N-benzoyl aziridine and the like. Examples of suitable N-substituted azetidines include N-tosyl azetidine, N-methanesulfonyl azetidine, N-trifluoromethanesulfonyl azetidine and the like.

Thus prepared, the polyamine dendrimers and other dense star polyamines can be reacted with a wide variety of compounds to produce the polyfunctional compounds having the unique characteristics that are attributable to the structure of the dendrimer. For example, a dendrimer having terminal amine moieties, may be reacted with an unsaturated nitrile to yield a polynitrile (nitrile-terminated) dendrimer. Alternatively, the polyamine dendrimer may be reacted with (1) an $\alpha\beta$-ethylenically unsaturated amide to form a polyamide (amide-terminated) dendrimer, (2) an $\alpha\beta$-ethylenically unsaturated ester to form a polyester (ester-terminated) dendrimer, (3) an ethylenically unsaturated sulfide to yield a polymercapto (thiol-terminated) dendrimer, or (4) an alkylene oxide to produce a hydroxy-terminated dendrimer and then with thionyl chloride to form a chloro-terminated dendrimer or with a tosylate to form a tosyl-terminated dendrimer. The tosyl- and chloro-terminated dendrimers are examples of electrophile-terminated dendrimers. The chloro-terminated dendrimer can be reacted with trialkyl sodiomethane tricarboxylate to form tricarboxyester-terminated dendrimers. An ester (alkoxycarbonyl)-terminated dendrimer such as (2) above or derived from halocarboxylic acid, can be reacted with alkanolamines such as diethanolamine, aminoethylethanolamine, or tris(hydroxymethyl)aminoethane to produce hydroxy-terminated dendrimers.

In addition, the dendrimer may be reacted with an appropriate difunctional or trifunctional compound such as an organo polyhalide, e.g., 1,4-dichlorobutane; polyesters such as poly(methyl acrylate); polyethers such as polyepichlorohydrin or polyisocyanate or polyisothiocyanate such as toluene diisocyanate, methylene diphenylene diisocyanate and polymers thereof (so-called MDI and polymeric MDI) and other aromatic polyisocyanates, aliphatic polyisocyanates, and polyisothiocyanates corresponding to the aforementioned polyisocyanates, to form a poly(dendrimer) or bridged dendrimer having a plurality of dendrimers linked together through the residues of the polyhalide, polyester, polyether or polyisocyanate. The bridged dendrimers can also be prepared by combining stoichiometric amounts of amine-terminated dendrimers of this invention with ester-terminated dendrimers of this invention or those described in U.S. Pat. No. 4,507,466. Dendrimer bridging also results when amine-terminated dendrimer is mixed with aziridine-terminated dendrimer under reaction conditions.

What is claimed is:

1. In a substance having at least one aperture of a diameter of about 10,000 Angstroms or less, a process for measuring and characterizing the diameter of said aperture, comprising:
   (a) contacting said substance with a solution of a plurality of dense star polymers having at least one core branch emanating from a core, each core branch having at least one terminal group provided that (1) the ratio of terminal groups to the branches emanating from the core is 2:1 or greater, (2) the density of terminal groups in the dense star polymer is at least 1.5 times that of an extended conventional star polymer having similar core and monomeric moieties and a comparable molecular weight and number of core branches wherein each of such branches of the extended conventional star polymer bears only one terminal group, (3) a molecular volume that is equal to or less than 80 percent of the molecular volume of said extended conventional star polymer, and (4) the two-dimensional molecular diameter of the dense star polymer is in the range from about 8 to about 10,000 Angstroms;
   (b) passing through or into said aperture at least one dense star polymer having a molecular diameter of about equal to or less than the diameter of said aperture; and
   (c) calculating the diameter of said aperture from measurements of either those dense star polymers passing therethrough or thereinto said aperture, of those dense star polymers not passing therethrough or thereinto, or of the combined measurements of those dense star polymers passing therethrough or thereinto said aperture and those not passing therethrough or thereinto.

2. The process of claim 1 wherein the dense star polymer has (1) at least 2 core branches per core, (2) a terminal group density at least 5 times that of the corresponding extended conventional star polymer, (3) a molecular volume that is equal to or less than 60 percent of the volume of the extended conventional star polymer, and (4) the two-dimensional molecular diameter of the dense star polymer is in the range from about 8 to about 500 Angstroms.

3. The process of claim 1 wherein the core of the dense star polymer is derived from a nucleophilic compound.

4. The process of claim 3 wherein the nucleophilic compound is an amine having a plurality of amine hydrogens.

5. The process of claim 1 wherein the dense star polymer has at least 3 core branches per core.

6. The process of claim 1 wherein the dense star polymer is a covalently bridged dense star polymer.

7. The process of claim 1 wherein the dense star polymer is a dendrimer having a polyvalent core that is covalently bonded to at least 1 ordered dendritic branch which extends to two generations such that each dendritic branch has at least four terminal groups and a symmetrical structure.

8. A process of claim 7, wherein said dense star polymer is a covalently bridged dendrimer.

9. The process of claim 8, wherein the molecular diameter of said covalently bridged dendrimer is in the range of between about 40 Å and about 10,000 Å.

10. The process of claim 1 wherein said substance having at least one aperture is a synthetic membrane.

11. The process of claim 1 wherein said substance having at least one aperture is a natural membrane.

12. The process of claim 1 wherein said substance having at least one aperture is a discrete biological particle.

13. The process of claim 12 wherein said particle is a virus.

14. The process of claim 12 wherein said particle is a bacteria.

15. The process of claim 12 wherein said particle is a protein.

16. The process of claim 12 wherein said particle is a cell.

17. The process of claim 1 wherein said steps of (a) contacting, (b) passing therethrough or thereinto, and (c) calculating are performed using hyperfiltration procedures.

18. The process of claim 1 wherein said steps of (a) contacting, (b) passing therethrough or thereinto, and (c) calculating are performed using ultrafiltration procedures.

* * * * *

UNITED STATES PATENT AND TRADEMARK OFFICE
CERTIFICATE OF CORRECTION

PATENT NO. : 4,713,975

DATED : December 22, 1987

INVENTOR(S) : Donald A. Tomalia and Larry R. Wilson

It is certified that error appears in the above-identified patent and that said Letters Patent is hereby corrected as shown below:

Col. 2, line 25, "demensional" should read -- dimensional --.

Col. 4, line 21, "form" should read -- from --.

Col. 6, line 25, the formula should read

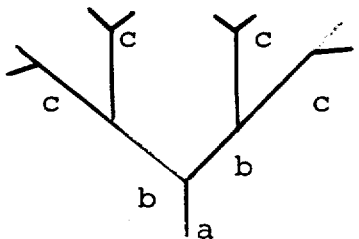

Col. 6, line 54, "acetylenly" should read -- acetylenyl --.

Col. 7, line 10, "groups" should be inserted after "activator".

UNITED STATES PATENT AND TRADEMARK OFFICE
CERTIFICATE OF CORRECTION

PATENT NO. : 4,713,975

DATED : December 22, 1987

INVENTOR(S) : Donald A. Tomalia and Larry R. Wilson

It is certified that error appears in the above-identified patent and that said Letters Patent is hereby corrected as shown below:

Col. 8, in the table, the 4th heading, "Materials Retained" should read -- Material Retained --.

Col. 7, in the table, the first line, under the heading "Concept", "Concentration" should read -- Concentrate --.

Col. 8, in the table, the second line, under the heading "Driving Force", a comma should be inserted after "difference".

Col. 7, in the table, under the heading "Concept", "Concentration" in the second occurrence should read -- Concentrate --.

Col. 8, in the table, under the heading "Driving Force", a comma should be inserted after "difference" in the second occurrence.

Col. 10, in the table, under the heading "Driving Force", the second line, a comma should be inserted after "difference".

UNITED STATES PATENT AND TRADEMARK OFFICE
CERTIFICATE OF CORRECTION

PATENT NO. : 4,713,975

DATED : December 22, 1987

INVENTOR(S) : Donald A. Tomalia and Larry R. Wilson

It is certified that error appears in the above-identified patent and that said Letters Patent is hereby corrected as shown below:

Col. 12, line 31, "procedure" should read -- procedures --.

Col. 15, line 2, that portion of the formula reading

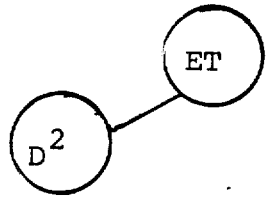

should read

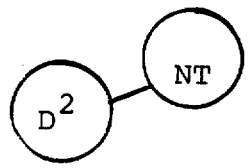

Col. 16, line 60, "$(NH_2)_1$" should read -- $(NH_2)_{11}$ --.

UNITED STATES PATENT AND TRADEMARK OFFICE
CERTIFICATE OF CORRECTION

PATENT NO. : 4,713,975

DATED : December 22, 1987

INVENTOR(S) : Donald A. Tomalia and Larry R. Wilson

It is certified that error appears in the above-identified patent and that said Letters Patent is hereby corrected as shown below:

Col. 17, line 25, "$\cong 300,00$" should read -- $\cong 300,000$ --.

Col. 17, line 27, "$\cong \overset{\circ}{A}$" should read -- $\cong 50 \overset{\circ}{A}$ --.

Col. 17, line 28, "$\equiv 100,000$" should read -- $\cong 100,000$ --.

Col. 17, line 30, "Us" should read -- Using --.

Col. 23, line 8, "prefperably" should read -- preferably --.

Col. 24, line 17, "each" should be inserted after "Zc".

Col. 24, line 32, a comma should be inserted after "compound".

UNITED STATES PATENT AND TRADEMARK OFFICE
CERTIFICATE OF CORRECTION

PATENT NO. : 4,713,975

DATED : December 22, 1987

INVENTOR(S) : Donald A. Tomalia and Larry R. Wilson

It is certified that error appears in the above-identified patent and that said Letters Patent is hereby corrected as shown below:

Col. 25, line 26, the formula should read

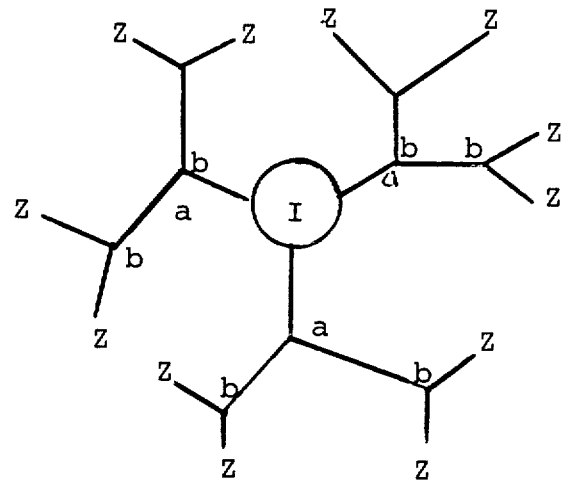

UNITED STATES PATENT AND TRADEMARK OFFICE
CERTIFICATE OF CORRECTION

PATENT NO. : 4,713,975
DATED : December 22, 1987
INVENTOR(S) : Donald A. Tomalia and Larry R. Wilson It is certified that error appears in the above-identified patent and that said Letters Patent is hereby corrected as shown below:

Col. 26, line 63, "rom" should read -- from --.

Col. 26, line 66, a comma should be inserted after "alkyl".

Col. 27, line 65, "are made reactive" should read -- the --.

Col. 28, line 1, that portion of the formula should read $$T' \longrightarrow [U\textcircled{Z}_y]_n \quad .$$

Col. 29, line 26, "αβ" should read -- α,β --.

Col. 29, line 28, "αβ" should read -- α,β --.

Signed and Sealed this

Twentieth Day of September, 1988

Attest:

DONALD J. QUIGG

*Attesting Officer*   *Commissioner of Patents and Trademarks*